US012564712B2

(12) United States Patent
Ko

(10) Patent No.: US 12,564,712 B2
(45) Date of Patent: Mar. 3, 2026

(54) HANDPIECE FOR TREATMENT, TREATMENT DEVICE INCLUDING SAME, AND METHOD FOR CONTROLLING TREATMENT DEVICE

(71) Applicant: LUTRONIC CORPORATION, Goyang-si (KR)

(72) Inventor: Kwang Chon Ko, Paju (KR)

(73) Assignee: LUTRONIC CORPORATION, Goyang-si (KR)

( * ) Notice: Subject to any disclaimer, the term of this patent is extended or adjusted under 35 U.S.C. 154(b) by 832 days.

(21) Appl. No.: 17/416,386

(22) PCT Filed: Dec. 6, 2019

(86) PCT No.: PCT/KR2019/017171
§ 371 (c)(1),
(2) Date: Jun. 18, 2021

(87) PCT Pub. No.: WO2020/130439
PCT Pub. Date: Jun. 25, 2020

(65) Prior Publication Data
US 2022/0072299 A1 Mar. 10, 2022

(30) Foreign Application Priority Data
Dec. 20, 2018 (KR) .......................... 10-2018-0166032

(51) Int. Cl.
*A61B 18/14* (2006.01)
*A61N 1/05* (2006.01)
*A61N 1/40* (2006.01)

(52) U.S. Cl.
CPC ............. *A61N 1/0502* (2013.01); *A61N 1/40* (2013.01)

(58) Field of Classification Search
CPC ... A61B 18/14; A61B 18/1477; A61B 18/148; A61B 18/1482; A61B 2018/0016; A61B 2018/143; A61B 2018/00291; A61B 2018/00452; A61B 2018/1475; A61B 2018/00196; A61B 2018/1425; A61N 1/0502; A61N 1/36017; A61N 1/40; A61H 9/00; A61H 9/0057
(Continued)

(56) References Cited

U.S. PATENT DOCUMENTS

| | | | | |
|---|---|---|---|---|
| 2008/0091183 A1* | 4/2008 | Knopp | ............... | A61B 18/1402 606/31 |
| 2009/0093864 A1* | 4/2009 | Anderson | .......... | A61B 18/1477 607/99 |
| 2012/0158100 A1* | 6/2012 | Schomacker | ...... | A61B 18/1477 607/101 |

FOREIGN PATENT DOCUMENTS

| | | |
|---|---|---|
| KR | 20070116253 A | 12/2007 |
| KR | 20110000790 A | 1/2011 |

(Continued)

*Primary Examiner* — Thomas A Giuliani

(57) ABSTRACT

A method for controlling a treatment device according to an embodiment of the present invention comprises the steps of: providing negative pressure between an insertion portion and a tissue surface such that the tissue surface positioned in front of the insertion portion is pulled toward the insertion portion; allowing at least a part of the insertion portion to be inserted into a tissue through the tissue surface; providing positive pressure to the tissue surface such that the tissue surface is pushed away from the insertion portion; and allowing a front end of the insertion portion to be extracted from the tissue surface.

9 Claims, 9 Drawing Sheets

(58) Field of Classification Search
USPC ............ 606/32, 34, 41, 42; 607/98, 99, 101,
607/113, 115, 116
See application file for complete search history.

(56) References Cited

FOREIGN PATENT DOCUMENTS

| | | | |
|---|---|---|---|
| KR | 10118710 | B1 | 10/2012 |
| KR | 20150128457 | A | 11/2015 |
| KR | 20170015951 | A | 2/2017 |
| KR | 20180055389 | A | 5/2018 |
| KR | 20180101763 | A | 9/2018 |
| WO | WO2006097925 | A1 | 9/2006 |
| WO | WO2012144713 | A1 | 10/2012 |
| WO | WO2018093190 | A1 | 5/2018 |
| WO | WO2018164423 | A1 | 9/2018 |

* cited by examiner

HANDPIECE FOR TREATMENT, TREATMENT DEVICE INCLUDING SAME, AND METHOD FOR CONTROLLING TREATMENT DEVICE

CROSS REFERENCE TO RELATED APPLICATIONS

This application claims priority to PCT Patent Application No. PCT/KR2019/017171, filed on Dec. 6, 2019, which claims priority to KR Application No. 10-2018-0166032, filed on Dec. 20, 2018, which are hereby incorporated by reference in its entirety.

TECHNICAL FIELD

The present disclosure relates to a handpiece for treatment, a treatment device including the handpiece, and a method for controlling the treatment device and, more particularly, to a handpiece for treatment that is inserted into the tissue of a human body to perform treatment through an invasive method, an RF treatment device including the handpiece, and a method for controlling the RF treatment device.

BACKGROUND ART

A method of treating tissue may be classified into a method of treating tissue from outside the tissue, and an invasive treatment method in which a part or all of a treatment device is inserted into the tissue to perform treatment. Among them, the invasive treatment method usually uses a treatment device having an insert part of a small diameter, such as a needle or a catheter, and treatment is performed after the treatment device is inserted to a target position in the tissue.

Such an invasive treatment method includes various treatment procedures, for example, a procedure of delivering a therapeutic substance into tissue, a procedure of performing surgical treatment through a mechanical operation while it is adjacent to specific tissue in the tissue, and a procedure of delivering energy to a target position in the tissue. Such a treatment method is disclosed in Korean Patent Laid-Open Publication No. 10-2011-0000790, and is applied in various ways.

In the invasive treatment method, an RF treatment method in which a part or all of an RF electrode is inserted into tissue to transfer RF energy uses a principle in which, when RF current flows through the electrode to the tissue, the tissue acts as resistance and thermal energy is generated.

However, in the case of performing the invasive treatment for soft skin tissue, while a front end of a needle is inserted into a surface of the tissue, the soft skin tissue is pressed by the front end of the needle, so that the needle may not be inserted into a dermal layer. Further, in a state where the front end of the needle reaches an epidermal layer, RF energy is released, thus possibly causing the side effect of denaturing the epidermal layer.

Furthermore, in the case of treating skin using the RF energy, the skin tissue may often adhere to the needle due to the RF energy. In this case, if the needle is removed with the skin tissue adhering to the needle, the skin may move with the needle when the needle is removed, thus causing the skin to be torn or causing excessive bleeding.

DISCLOSURE

Technical Problem

The present disclosure is to provide a handpiece for treatment, an RF treatment device, and a method for controlling the treatment device, capable of inserting a front end of a needle to an intended depth in skin tissue, and minimizing damage to the skin tissue which may occur while the needle is removed from the skin tissue.

Technical objects to be achieved by the present disclosure are not limited to the aforementioned technical objects, and other technical objects not described above may be evidently understood by a person having ordinary skill in the art to which the present disclosure pertains from the following description.

Technical Solution

In order to solve the aforementioned problem, the present disclosure proposes a handpiece for treatment including a housing having at least one through hole formed in a front end thereof, an insertion portion inserted through a tissue surface of a treatment site into tissue in a state where at least a part of the insertion portion is exposed through the through hole, and a pressure providing channel pulling the treatment site towards the through hole by transmitting negative pressure to a front surface of the through hole, and pushing the treatment site, pulled towards the through hole, away from the through hole by transmitting positive pressure to the front surface of the through hole.

In order to solve the aforementioned problem, the present disclosure proposes an RF treatment device including a body having an RF generator and a pressure generator, and a handpiece connected to the body, wherein the handpiece includes a housing having at least one through hole formed in a front end thereof, an insertion portion inserted through a tissue surface of a treatment site into tissue and applying RF energy transferred from the RF generator into the tissue in a state where at least a part of the insertion portion is exposed through the through hole, and a pressure providing channel pulling the treatment site towards the through hole by transmitting negative pressure provided by the pressure generator to a front surface of the through hole, and pushing the treatment site, pulled towards the through hole, away from the through hole by transmitting positive pressure provided by the pressure generator to the front surface of the through hole.

In order to solve the aforementioned problem, the present disclosure proposes a method for controlling a treatment device including providing negative pressure between an insertion portion and a tissue surface such that the tissue surface positioned in front of the insertion portion is pulled toward the insertion portion, allowing at least a part of the insertion portion to be inserted into tissue through the tissue surface, providing positive pressure to the tissue surface such that the tissue surface is pushed away from the insertion portion, and allowing a front end of the insertion portion to be extracted from the tissue surface.

Other specific details of the present disclosure are included in the detailed description and drawings.

Advantageous Effects

Embodiments of the present disclosure at least have the following effects.

It is possible to insert a front end of a needle to an intended depth in skin tissue and to minimize damage to skin tissue which may occur while the needle is removed from the skin tissue.

Effects obtained by the present disclosure are not limited to the aforementioned effects, and various other effects are involved in the present disclosure.

BEST MODE

Figure 1:
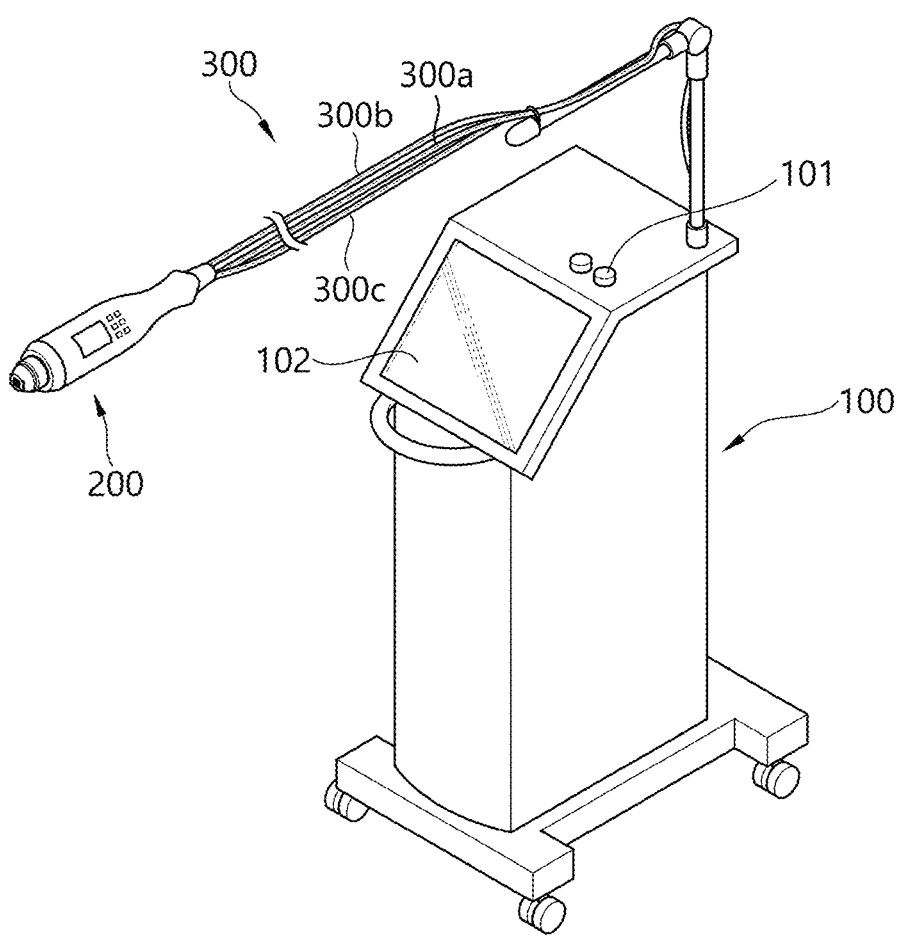
FIG. 1 is a perspective view illustrating an RF treatment device in accordance with an embodiment of the present disclosure.

The above and other objectives, features, and other advantages of the present disclosure will be more clearly understood from the following detailed description when taken in conjunction with the accompanying drawings. However, the disclosure may be embodied in different forms without being limited to the embodiments set forth herein. Rather, the embodiments disclosed herein are provided to make the disclosure thorough and complete and to sufficiently convey the spirit of the present disclosure to those skilled in the art. The present disclosure is to be defined by the claims.

Further, embodiments set forth herein will be described with reference to sectional views and/or schematic views that are ideal exemplary views of the present disclosure. Thus, the exemplary views may be modified by manufacturing technology and/or tolerance. Furthermore, the size or shape of components shown in the drawings may be exaggerated for the clarity and convenience of description. The same reference numerals are used throughout the drawings to designate the same or similar components.

Hereinafter, the term "RF treatment device" covers all devices for treating humans as well as animals such as mammals. The treatment device may include various devices that transfer RF energy for the purpose of improving the condition of a lesion or tissue. Although a device for treating a skin lesion will be mainly described in the following embodiment, the present disclosure is not limited thereto. That is, it is to be understood that the treatment device may be applied to various devices that transfer RF energy to various affected areas, including a device for surgically treating internal organ lesions.

Hereinafter, the term "treatment" refers to remodeling in which RF energy is transferred to tissue including collagen to change the state of the tissue into at least one of coagulation or ablation, and may be treatment for at least one of wrinkles, tone and textural changes, scars and acne scarring, sagging mucosa, overall rejuvenation, hyperhidrosis, laxity, lifting, tightening, and fat reduction for skin tissue, for example.

Hereinafter, the term "tissue" refers to the assembly of cells constituting various body organs of animals including humans, and covers various tissues forming various internal organs as well as skin tissue.

Hereinafter, the term "insertion portion" refers to a component of the treatment device that is inserted into tissue. This is a structure that has a pointed end and is thin and long, such as a needle, a microneedle, or a catheter, and includes various configurations that are inserted through the surface of tissue to the interior of the tissue.

Hereinafter, an RF treatment device and a treatment method using the RF treatment device and/or a control method of the RF treatment device according to an embodiment of the present disclosure will be described with reference to the

DRAWINGS

Figure 2:
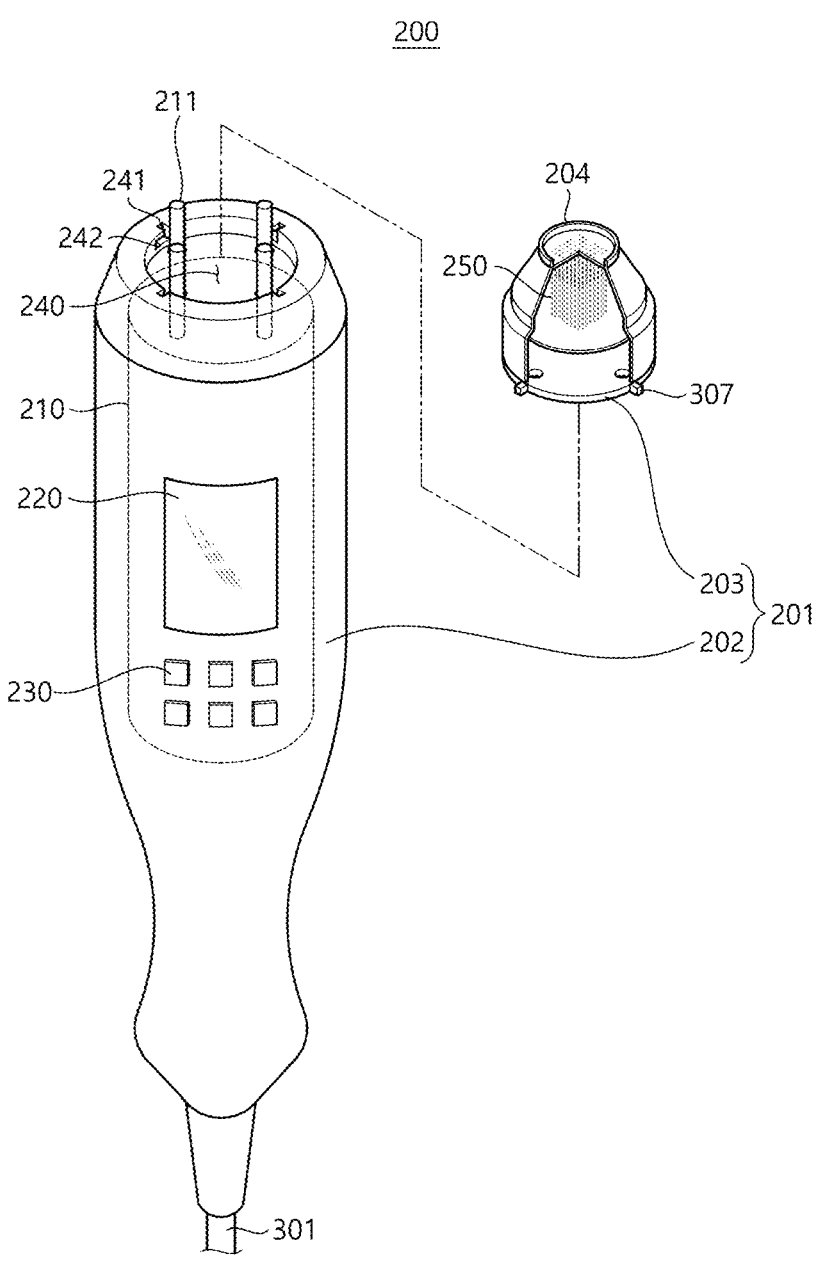
FIG. 2 is an exploded perspective view illustrating a handpiece of the RF treatment device of FIG. 1.
Figure 3:
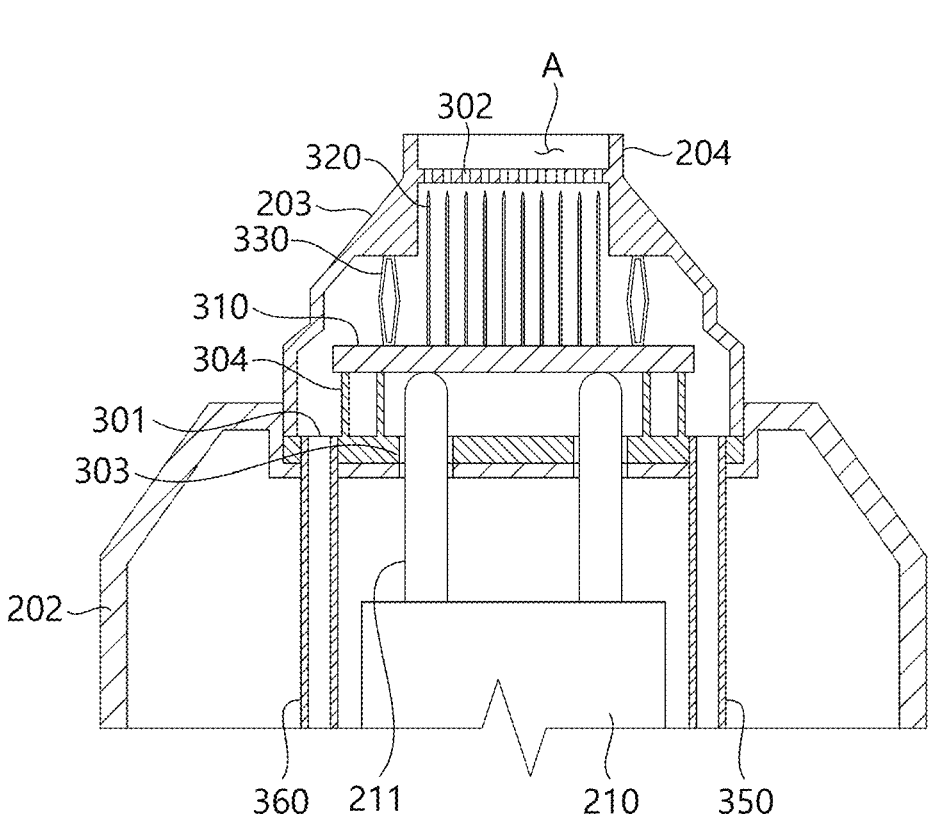
FIG. 3 is a sectional view schematically illustrating the internal structure of a front end of the handpiece of FIG. 2.

FIG. 1 is a perspective view illustrating an RF treatment device in accordance with an embodiment of the present disclosure, FIG. 2 is an exploded perspective view illustrating a handpiece of the RF treatment device of FIG. 1, and FIG. 3 is a sectional view schematically illustrating the internal structure of a front end of the handpiece of FIG. 2.

As shown in FIG. 1, a medical RF device according to this embodiment is composed of an RF treatment device. Such an RF treatment device 1 includes a body 100, and a handpiece 200 that may be used for treatment with it being held by a user.

An RF generator 111 (see FIG. 4) may be provided in the body 100. The RF generator 111 generates RF energy used for treatment. The RF generator 111 is configured to generate and transfer the RF energy not in a continuous waveform but in a pulse form. The RF generator 111 may generate RF pulses of various parameters (e.g. output, pulse duration, pulse interval, frequency, etc.) according to a patient's constitution, a treatment purpose, or a treatment site. The RF pulse generated in the RF generator of this embodiment is a therapeutic RF pulse used for the purpose of treating tissue. The RF energy used for treating the skin may be adjusted in the range of 0.1 to 0.8 MHz.

Furthermore, a pressure generator may be provided inside and/or outside the body 100. The pressure generator may include a negative-pressure generator 112 (see FIG. 4) and a positive-pressure generator 113 (see FIG. 4).

The negative-pressure generator 112 may include components that may create a pressure atmosphere lower than atmospheric pressure, for instance, a vacuum pump. The vacuum pump may be provided in the body 100. The positive-pressure generator 113 may include components that may create a pressure atmosphere higher than atmospheric pressure, for instance, an air tank. The air tank may be provided inside or outside the body 100.

Although the vacuum pump has been proposed as an example of the negative-pressure generator 112 and the air tank has been proposed as an example of the positive-pressure generator 113, other components may be used as the negative-pressure generator 112 as they may suck gas, and other components may be used as the positive-pressure generator 113 as they may supply gas.

Alternatively, the negative-pressure generator 112 and the positive-pressure generator 113 may be configured with one component using a motor that may rotate forwards and backwards. In other words, through a configuration in which a motor and a fan are coupled, gas may be sucked when the motor rotates in one direction, and gas may be supplied when the motor rotates in the other direction.

A switch 101 for adjusting the operation of the treatment device, e.g., the operation of turning on or off a power supply, and a display unit 102 for displaying various pieces of information including the operation of the treatment device may be included on the outer surface of the body 100. Such a display unit 102 may be formed of a touch screen to display various pieces of information, and may be configured such that a user may directly set treatment contents through the display unit 102.

The handpiece 200 is connected to the body via a connector 300.

As shown in FIG. 1, the connector 300 may include a first connector 300a, a second connector 300b, and a third connector 300c.

The first connector 300a may transmit power or a control signal required to operate various devices of the handpiece 200 from the body 100. The connector 300 may be formed of a cable including various signal lines and power lines, or may have a bent structure to be easily bent by a user's manipulation.

The second connector 300b connects the negative-pressure generator 112 and the handpiece 200. To be more specific, the second connector 300b connects the negative-pressure generator 112 and a negative-pressure providing channel 360 of the handpiece 200 to transmit negative pressure from the negative-pressure generator 112 to the negative-pressure providing channel 360. To be more specific, as the negative-pressure generator 112 operates, the second connector 300b transmits air sucked through the negative-pressure providing channel 360 to the negative-pressure generator 112.

The third connector 300c connects the positive-pressure generator 113 and the handpiece 200. To be more specific, the third connector 300c connects the positive-pressure generator 113 and a positive-pressure providing channel 350 of the handpiece 200 to transmit positive pressure from the positive-pressure generator 113 to the positive-pressure providing channel 350. To be more specific, as the positive-pressure generator 113 operates, the third connector 300c provides air to the positive-pressure providing channel 350.

According to an embodiment, when the negative-pressure generator 112 and the positive-pressure generator 113 are not separate components but are formed as a single component, the second connector 300b and the third connector 300c may also be formed as a single connector. In other words, the connector 300 may be composed of the first connector 300a and the second connector that provides positive pressure/negative pressure.

As shown in FIG. 2, a housing 201 of the handpiece 200 may include a handpiece body 202 and a tip 203 that are detachably coupled to each other.

A handpiece operating portion 230 and a handpiece display portion 220 may be provided on an outer surface of the handpiece body 202. The handpiece operating portion 230 may be configured to control the on/off of the handpiece 200, adjust the insertion depth of the insertion portion 250, or adjust the intensity of the energy transferred through the insertion portion 250. The display portion 220 of the handpiece may display various pieces of information required in a setting mode or during treatment to a user. Thus, a user may perform treatment by operating the operating portion 230 with the handpiece 200 being held by his or her hand, and simultaneously may check treatment contents easily through the display portion 220.

A driving portion 210 is installed in the handpiece 200. The driving portion 210 is configured to move the insertion portion 250, thus allowing the insertion portion to be selectively inserted into tissue. Such a driving portion 210 may be formed using a solenoid, various linear actuators such as a hydraulic/pneumatic cylinder, a linear motor, etc. By way of example, the driving portion of this embodiment is configured to linearly move an output terminal 211 provided on an end of the handpiece in a longitudinal direction. A plurality of needles 320 corresponding to the insertion portion 250 is disposed on an end of the output terminal 211, so that the insertion portion 250 is ejected and retracted through an end (end coming into contact with a treatment site) of the handpiece 200 as the output terminal moves linearly. As such, as the insertion portion 250 is moved forwards/backwards by the driving of the driving portion 210, the insertion portion may be inserted into a patient's tissue or be withdrawn from the tissue.

As described above, the insertion portion 250 is a component that is inserted through a tissue surface into the tissue, and is provided in the handpiece 200. Although the insertion portion 250 of this embodiment is composed of a microneedle 320 that is easy to be inserted into the tissue, the insertion portion may be formed of various structures such as a single needle structure or a catheter. The microneedle 320 of this embodiment may be a needle having the diameter ranging from several micrometers to several thousand micrometers (μm), and preferably may use a needle having a diameter ranging from 10 to 1000 μm.

The insertion portion 250 is a component that is inserted into a patient's tissue, and may cause problems in terms of sanitation if the insertion portion is repeatedly used. Therefore, the insertion portion 250 of this embodiment is provided on the tip 203 that is detachably attached to the end of the handpiece body 202, and the tip 203 may be replaced with a new one after treatment.

Specifically, a detachment protrusion 307 is formed on an outer wall of a base 301 defining the lower surface of the tip 203 to protrude outwards. A guide groove 241 for guiding the entry of the detachment protrusion 307 and a removal prevention groove 242 for preventing the removal of the detachment protrusion 307 entering the guide groove 241 are formed in a recess portion 240 to which the tip 203 is coupled. Further, the detachment protrusion 307 of the tip 203 is guided along the guide groove 241 to be fastened to the removal prevention groove 242, so that the tip is installed in the handpiece. However, the coupling structure of the handpiece body 202 and the tip 203 shown in FIG. 2 is an example of a structure where the tip 203 is detachably installed in the handpiece body 202, and the coupling structure of the handpiece body 202 and the tip 203 may be changed in various ways. Furthermore, the tip 203 may be integrally formed in the handpiece body 202.

The tip 203 is configured such that the insertion portion 250 composed of a plurality of microneedles 320 is installed therein, and is detachably installed in the recess portion 240 that is provided on an end of the body of the handpiece 200. The rear surface of the tip 203 is provided with a plurality of holes (not shown) into which the above-mentioned output terminal 211 may be selectively inserted. Therefore, as the above-described output terminal 211 moves forwards/backwards, the plurality of microneedles 320 accommodated in the tip 203 also moves forwards/backwards. Further, if the tip 203 is installed in the recess portion 240, the microneedles 230 of the tip 203 may be electrically connected to an RF circuit in the handpiece 200 to transfer the RF energy through the microneedles 320 into the tissue at the treatment position.

An RF transfer portion 310 in which the plurality of needles 320 is installed is provided in the tip 230. The plurality of needles 320 is fixedly installed in the RF transfer portion 310 in a matrix form. An electric circuit is formed in the RF transfer portion 310 to be connected to each of the needles 320. The electric circuit formed in the RF transfer portion 310 is electrically connected to the output terminal 211 to allow the RF energy transferred through the output terminal 211 to be transferred through the RF transfer portion 310 to the plurality of needles 320.

A front end of the tip 230 may form a portion that is adjacent to or is in contact with a patient's skin during treatment, and a plurality of through holes 302 is formed in the front end of the tip 230 to allow the plurality of needles 320 to be ejected and retracted therethrough.

At least one hole 303 is provided in a lower portion of the tip 230 to allow the output terminal 211 to pass therethrough. When the driving portion 210 is operated, the output terminal 211 linearly moves along the hole 303 to press the RF transfer portion 310. A rear surface of the RF transfer portion 310 is seated in a support 304 provided in the tip 230, and a front surface of the RF transfer portion 310 is pressed by an elastic member 330 installed in the tip 230.

If the output terminal 211 moves to press the RF transfer portion 310, the RF transfer portion 310 moves forwards while being separated from the support 304, and the plurality of needles 320 is inserted into the skin tissue while protruding forwards from the through holes 302. Further, if the output terminal 211 is moved backwards by the driving of the driving portion 210, the RF transfer portion 310 is moved backwards by the restoring force of the elastic member 330, so that the plurality of needles 320 also returns to the interior of the tip 230. Although not shown in the drawings, a separate guide member for guiding a path along which the above-described RF transfer portion 310 moves may be further provided.

Although not shown in the drawings, the circuit of the RF transfer portion 310 may be electrically connected to the RF generator 111 of the body 100 if the tip 230 is installed on the handpiece body 202. Alternatively, the circuit of the RF transfer portion 310 may be electrically connected to the RF generator 111 selectively when the circuit is pressed by the output terminal 211 (e.g., an electrode is formed on the end of the output terminal 211 to be electrically connected to the RF transfer portion 310 when it being pressed).

Each needle 320 may be composed of a microneedle having the diameter of about 5 to 500 μm. The needle 320 is formed of a conductive material to transfer the RF energy. A part of a surface of each needle excluding the front end thereof is formed of an insulating material to prevent the RF energy from being transferred to the tissue. Thus, a part of the front end of each needle serves as an electrode, and is configured to transfer the RF energy through only the front end to the tissue. Therefore, it is possible to selectively transfer the RF energy to a part at which the end of the needle is positioned during treatment.

In order to generate negative pressure/positive pressure on the front surface of the through hole 302 (i.e., treatment-site receiving space A), the handpiece 200 includes pressure providing channels 350 and 360. As shown in FIG. 3, the pressure providing channels 350 and 360 may include a negative-pressure providing channel 360 and a positive-pressure providing channel 350.

Each of the negative-pressure providing channel 360 and the positive-pressure providing channel 350 is provided in the handpiece body 202. Although not shown in the drawings, the rear end of the negative-pressure providing channel 360 is connected to the second connector 300b, and the rear end of the positive-pressure providing channel 350 is connected to the third connector 300c.

Furthermore, the front ends of the negative-pressure providing channel 360 and the positive-pressure providing channel 350 may be opened towards the interior of the tip 203. To be more specific, the front ends of the negative-pressure providing channel 360 and the positive-pressure providing channel 350 are opened to the internal space of the tip 203 communicating with the through hole 302.

Therefore, the negative pressure supplied from the negative-pressure generator 112 is transmitted through the negative-pressure providing channel 360 to the front surface of the through hole 302. That is, if the negative-pressure generator 112 operates, air in the front surface of the through hole 302 flows through the through hole 302 and the internal space of the tip 203 into the negative-pressure providing channel 360, and is transmitted through the negative-pressure providing channel 360 to the negative-pressure generator 112.

Furthermore, the positive pressure supplied from the positive-pressure generator 113 is transmitted through the positive-pressure providing channel 350 to the front surface of the through hole 302. In other words, if the positive-pressure generator 113 operates, gas supplied by the positive-pressure generator 113 is provided through the positive-pressure providing channel 350 to the interior of the tip 203, and then is sprayed onto the front surface of the through hole 302 through the through hole 302.

As shown in FIGS. 2 and 3, a protruding rim 204 is formed on the front end of the tip 203 and protrudes outwards to surround the through holes 302. The protruding rim 204 defines the treatment-site receiving space A along with the front end of the tip 203 in which the through holes 302 are formed.

If the front end of the tip 203 comes into close contact with the skin surface of the treatment site, the treatment-site receiving space A becomes a substantially closed space. Hence, if the negative-pressure generator 112 operates, gas in the treatment-site receiving space A flows through the negative-pressure providing channel 360, so that the treatment-site receiving space A takes a negative pressure atmosphere that is lower than atmospheric pressure. If the positive-pressure generator 113 operates, gas supplied through the positive-pressure providing channel 350 is introduced into the treatment-site receiving space A, so that the treatment-site receiving space A takes a positive pressure atmosphere that is lower than atmospheric pressure.

As shown in FIG. 3, the negative-pressure providing channel 360 and the positive-pressure providing channel 350 may be formed through the end of the base 301, and may be formed such that the front end of each channel is opened through a surface of the base 301. Although not shown in the drawings, according to another embodiment, the front ends of the negative-pressure providing channel 360 and the positive-pressure providing channel 350 may be positioned between the base 301 and the RF transfer portion 310.

In this case, since the negative-pressure providing channel 360 and the positive-pressure providing channel 350 are physically separated from the RF transfer portion 310 moving along with the needle 320 and are secured to the base 301 that is a fixed structure, the possibility of damage or removal is low in spite of the repeated driving of the driving portion 210 and the output shaft 211 and thereby stability is enhanced.

However, according to an embodiment, the negative-pressure providing channel 360 and the positive-pressure providing channel 350 may be configured so that they pass through the base 301 and the RF transfer portion 310 and then the front ends thereof are opened on a surface of the RF transfer portion 310 or are positioned between the RF transfer portion 310 and the through hole 302. In this case, since the front ends of the negative-pressure providing channel 360 and the positive-pressure providing channel 350 are positioned closer to the through hole 302 as compared to the embodiment of FIG. 3, it is possible to more effectively create the negative pressure/positive pressure atmosphere in the treatment-site receiving space A.

Alternatively, according to an embodiment, the negative-pressure providing channel 360 and the positive-pressure providing channel 350 are not formed in the handpiece body 202 but are formed outside the handpiece body 202, and the respective front ends thereof may pass through the side surface of the tip 203 so that the negative-pressure providing channel 360 and the positive-pressure providing channel 350 communicate with the interior of the tip 203.

In this case, when the tip 203 is replaced with a new one, the negative-pressure providing channel 360 and the positive-pressure providing channel 350 may be configured to be replaced along with the tip 203. Further, the tip 203 may be configured to be easily separated from/coupled to the negative-pressure providing channel 360 and the positive-pressure providing channel, thus making it easier to separate or couple the tip 203 from or to the negative-pressure providing channel 360 and the positive-pressure providing channel 350 when the tip 203 is replaced with a new one, as compared to the above-described embodiment.

Figure 4:
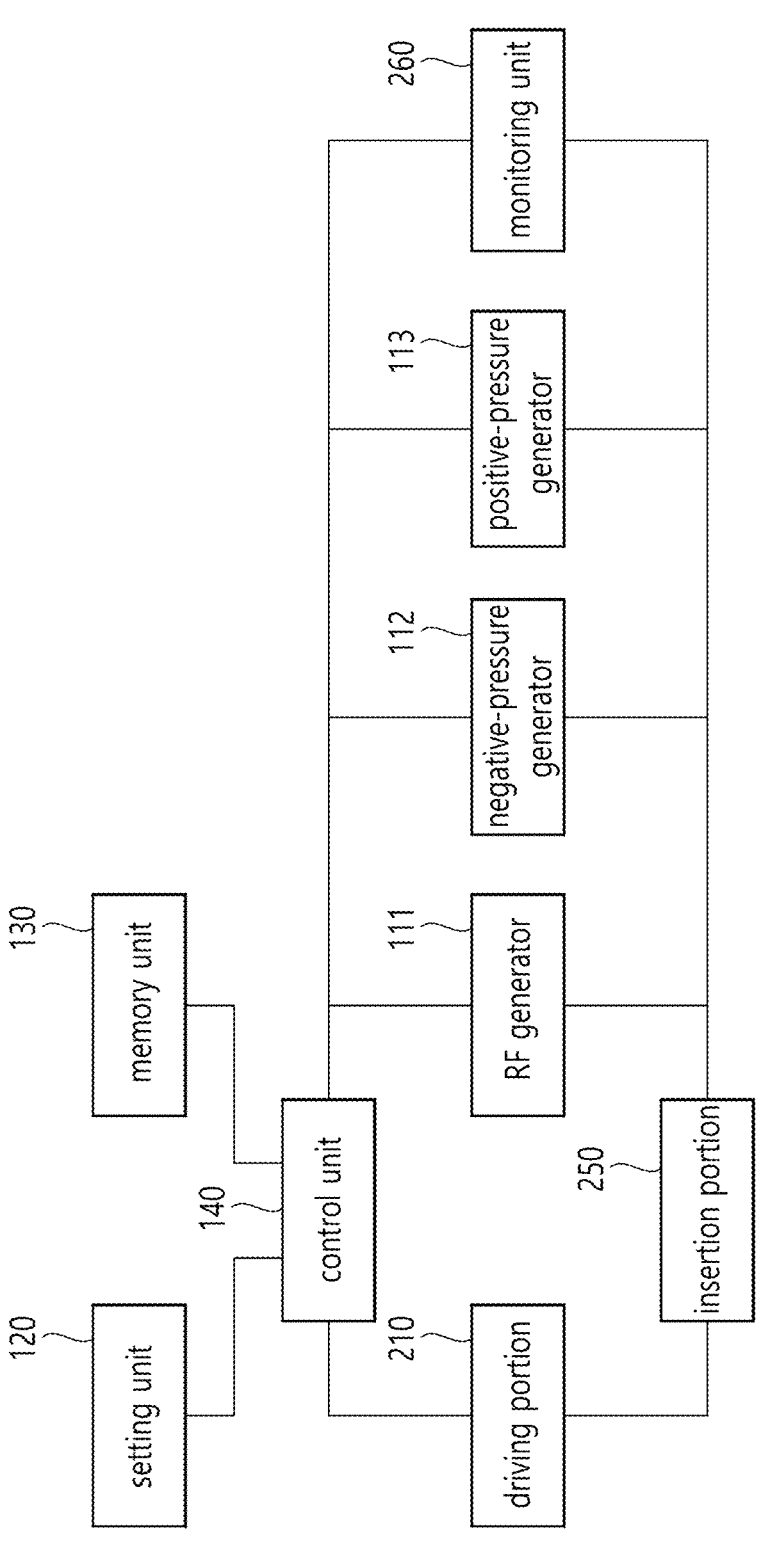
FIG. 4 is a block diagram illustrating a main control system of the RF treatment device of FIG. 1.

FIG. 4 is a block diagram illustrating a main control system of the RF treatment device of FIG. 1.

The control unit 140 is a component that may control the operation of various components of the body 100 and the handpiece 200. In other words, the control unit 140 may control the operation of the driving portion 210 of the handpiece to insert the insertion portion 250 into the tissue or withdraw the insertion portion from the tissue or adjust the insertion depth of the insertion portion 250.

Furthermore, the control unit 140 may control the RF generator 111 to adjust the on/off operation of the RF pulse and the parameter of the RF pulse. Thereby, the RF treatment device 1 may provide the RF pulse having an appropriate parameter, after inserting the microneedle into the tissue.

Furthermore, the control unit 140 may control the operation of the negative-pressure generator 112 and the positive-pressure generator 113 to control the operation timing of the negative-pressure generator 112 and the positive-pressure generator 113, the provided negative pressure/positive pressure, etc. To this end, the handpiece 200 may include a pressure sensor (not shown) that may sense the pressure of the interior of the tip 203 or the treatment-site receiving space A, the monitoring unit 260 may receive a signal sensed by the pressure sensor, and the control unit 140 may control the operation of the negative-pressure generator 112 and the positive-pressure generator 113 on the basis of information about pressure received by the monitoring unit 260.

The setting unit 120 is a component that allows a user to set treatment contents. Further, the control unit 140 controls various components to perform a treatment operation on the basis of the contents that are set through the setting unit 120.

The setting unit 120 may be composed of the above-described display unit 102 and/or a switch, and may perform a setting operation in a manner of displaying various options to a user through the display unit 102 and selecting a displayed option by the user.

Furthermore, the RF treatment device 1 further includes a memory unit in which various data is stored. The control unit 140 may perform a control operation by storing information required for controlling the RF treatment device in the memory unit or reading data stored in the memory unit 130.

Moreover, the RF treatment device further includes a monitoring unit 260. The monitoring unit 260 is a component for monitoring information about conditions of tissue corresponding to a treatment position during treatment. The monitoring unit 260 monitors the temperature of tissue, or monitors the impedance of the RF energy transfer path passing through the tissue, or monitors the pressure of the interior of the tip 203 or the treatment-site receiving space A, or monitors at least one of various pieces of information required for treatment, such as the contact of the handpiece or the pressed state.

For example, the monitoring unit 260 of this embodiment may be provided on a path where the RF energy is transferred, thus monitoring the impedance of the path where the RF energy is transferred after passing through the tissue. Such a monitoring unit may be provided on the RF transfer path in the handpiece, or be provided on the RF transfer path in the body. The monitoring unit 260 may monitor an impedance value by causing a separate test current to flow through the insertion portion 250, and may monitor an impedance value measured while the therapeutic RF pulse is transmitted. Since the measured impedance varies depending on the patient's characteristics or a change in condition of the tissue, it may be interpreted as "tissue impedance" for convenience. According to the present disclosure, the monitoring unit 260 may monitor the tissue impedance before or during treatment, and the treatment contents may be adjusted on the basis of the monitored impedance.

Figure 5:
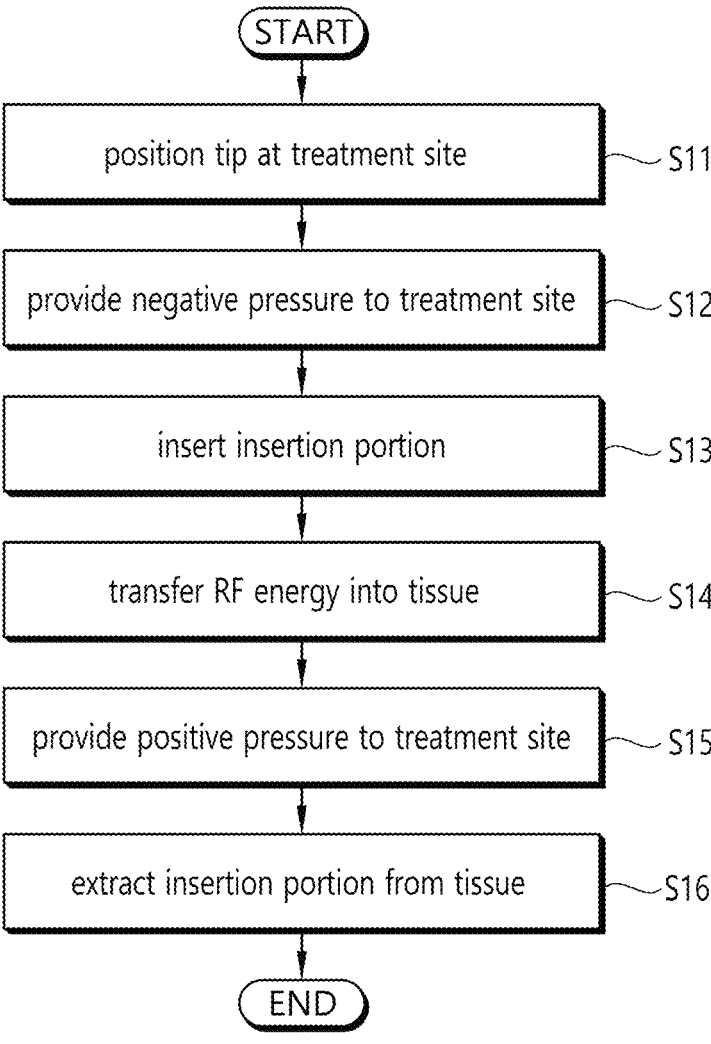
FIG. 5 is a diagram illustrating a treatment method using an RF treatment device and/or a method of controlling the RF treatment device in accordance with an embodiment of the present disclosure.

FIG. 5 is a diagram illustrating a treatment method using an RF treatment device and/or a method of controlling the RF treatment device in accordance with an embodiment of the present disclosure. FIGS. 6 to 9 are diagrams illustrating a treatment method using an RF treatment device and/or a method of controlling the RF treatment device in accordance with an embodiment of the present disclosure.

Figure 6:
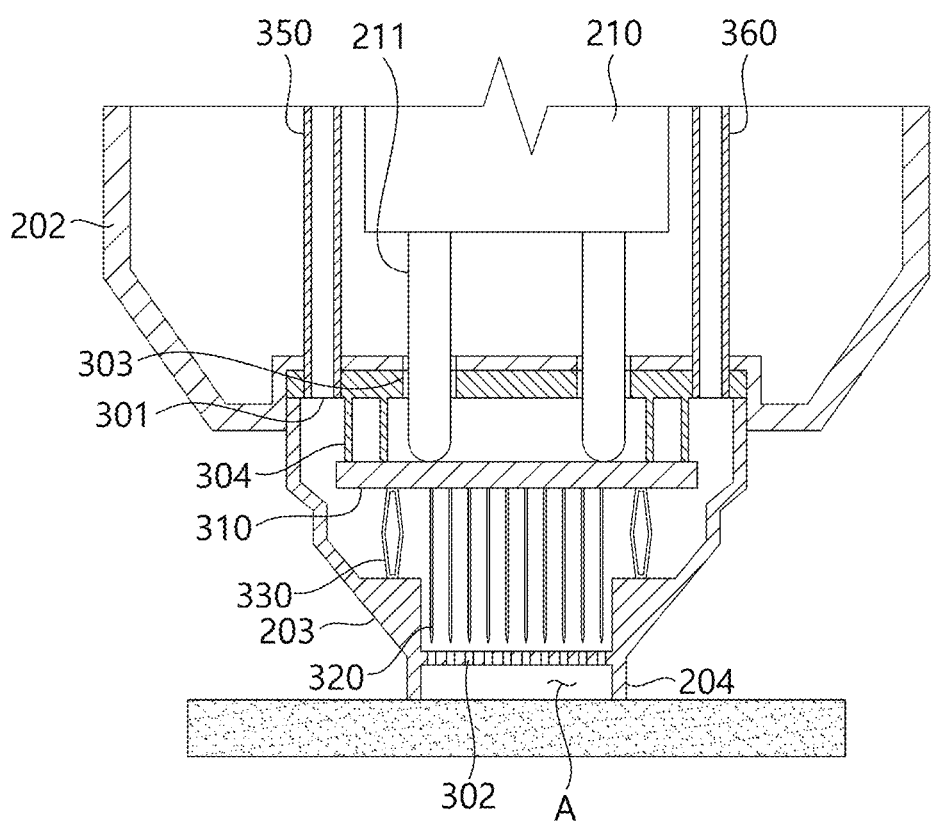
FIGS. 6 to 9 are diagrams illustrating a treatment method using an RF treatment device and/or a method of controlling the RF treatment device in accordance with an embodiment of the present disclosure.

First, the tip 203 of the handpiece 200 is positioned at the treatment site (S11). As shown in FIG. 6, the front end (tip) 203 of the handpiece 200 in which the insertion portion 250 is installed is positioned to be adjacent to or be in contact with the tissue surface of the treatment site.

Figure 7:
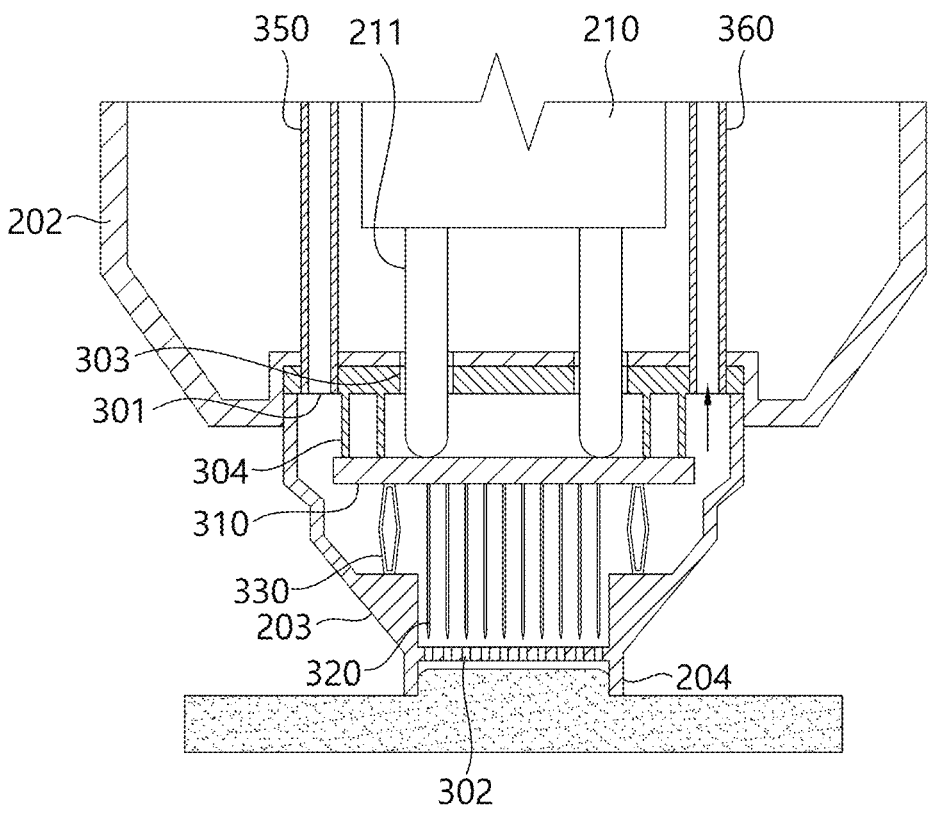

Subsequently, a step of providing the negative pressure to the treatment site is performed (S12). In response to a signal detecting a user's manipulation or detecting that the tip 203 of the handpiece 200 comes into contact with the tissue surface at the treatment site, the control unit 140 operates the negative-pressure generator 112. By the operation of the negative-pressure generator 112, air in the treatment-site receiving space A flows through the through hole 302 and the internal space of the tip 203 into the negative-pressure providing channel 360 (see the arrow of FIG. 7), so that the negative-pressure atmosphere is created in the treatment-site receiving space A. Since the negative pressure is generated between the through hole 302 and the tissue surface, as shown in FIG. 7, the tissue surface of the treatment site is pulled towards the through hole 302.

The monitoring unit 260 may be configured to monitor the pressure level of the treatment-site receiving space A and/or the internal space of the tip 203, and the control unit 140 may control the negative-pressure generator 112 on the basis of the pressure level monitored by the monitoring unit 260, thus allowing the negative pressure of the treatment-site receiving space A and/or the internal space of the tip 203 to be controlled to an appropriate level.

Simultaneously or subsequently, a step of inserting the insertion portion 250 into the tissue is performed (S13). The control unit 140 operates the driving portion 210 to move the insertion portion 250 forwards. In other words, the control unit 140 operates the driving portion 210, so that the front ends of the plurality of needles 320 pass through the through holes 302 and then pass through the surface of the tissue pulled towards the through holes 302 to be inserted into the tissue, as shown in FIG. 8.

Generally, the front end of the needle from which the RF energy is released should reach a dermal layer to effectively perform treatment. In the process of inserting the front end of the needle into the tissue surface, soft skin tissue is pressed by the front end of the needle, so that the needle may not be inserted to a sufficient depth. In this case, the RF energy is released with the front end of the needle reaching an epidermal layer, thus possibly causing the side effect of denaturing the epidermal layer.

Figure 8:
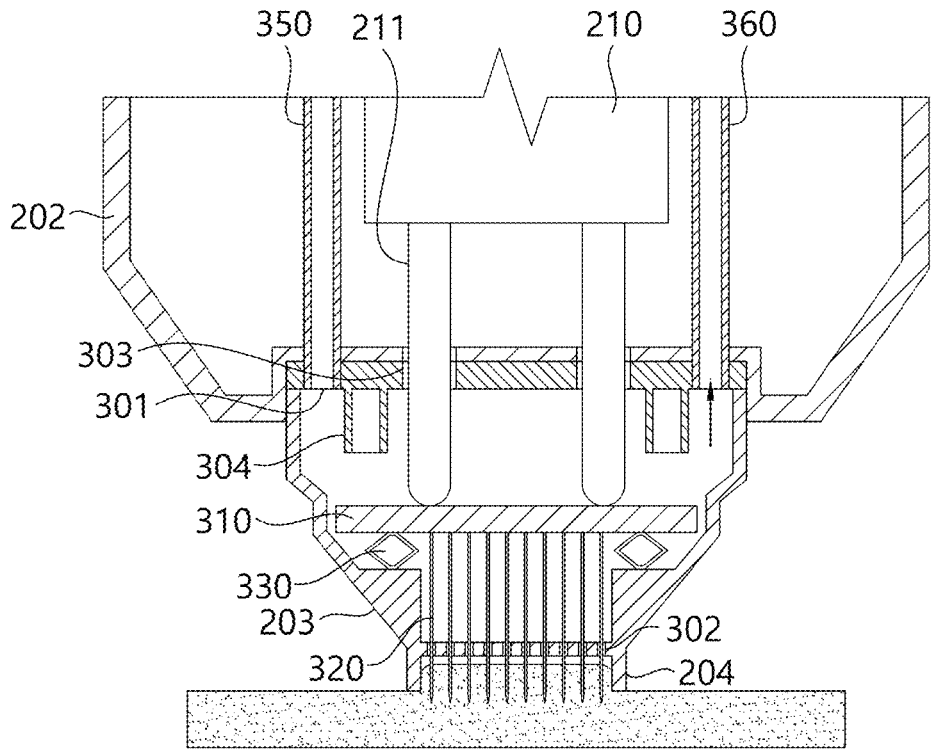

According to an embodiment of the present disclosure, as shown in FIG. 8, negative pressure is created between the tissue surface and the through hole 302. Thus, the front end of the needle 320 is inserted into the tissue with the tissue surface being pulled towards the through hole 302, so that the pressing of the soft skin tissue by the front end of the needle 320 is minimized in the process of inserting the front end of the needle 320 into the tissue surface, thus allowing the needle 320 to be inserted to a sufficient depth.

Thereafter, a step of transferring the RF energy into the tissue is performed (S14). The control unit 140 controls the RF generator 111 to transfer the RF energy through the first connector 300a, the output terminal 211, the RF transfer portion 310, and the plurality of needles 320 into the tissue.

Figure 9:
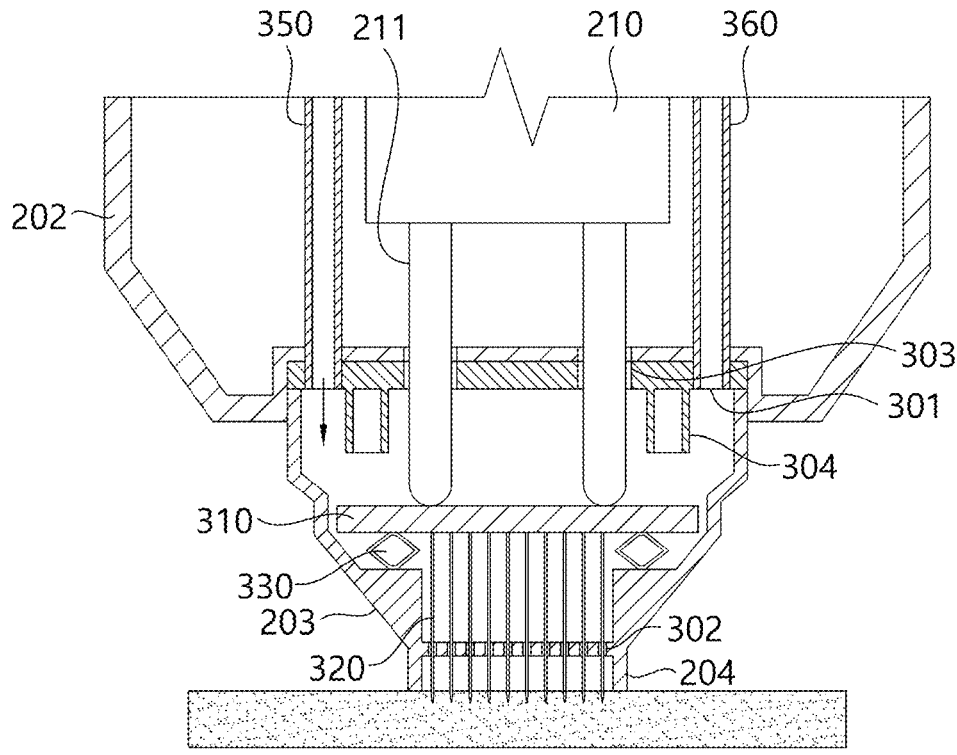

Subsequently, a step of providing the positive pressure to the treatment site is performed (S15). In response to a signal detecting a user's manipulation or detecting that the supply of the RF energy is cut off, the control unit 140 operates the positive-pressure generator 113. By the operation of the positive-pressure generator 113, gas is supplied through the positive-pressure providing channel 350 into the tip 203 (see the arrow of FIG. 9), so that positive-pressure atmosphere is created in the treatment-site receiving space A. Since the positive pressure is generated between the through hole 302 and the tissue surface, as shown in FIG. 9, the tissue surface of the treatment site is pushed away from the through hole 302.

The monitoring unit 260 may be configured to monitor the pressure level of the treatment-site receiving space A and/or the internal space of the tip 203, and the control unit 140 may control the positive-pressure generator 113 on the basis of the pressure level monitored by the monitoring unit 260, thus allowing the positive pressure of the treatment-site receiving space A and/or the internal space of the tip 203 to be controlled to an appropriate level.

Simultaneously or subsequently, a step of extracting the insertion portion 250 from the tissue is performed (S16). The control unit 140 operates the driving portion 210 to move the insertion portion 250 backwards. In other words, the control unit 140 operates the driving portion 210 to cause the front ends of the plurality of needles 320 to be pulled out of the surface of the tissue, thus completing the treatment.

Generally, in the case of treating skin using the RF energy, the skin tissue may often adhere to the needle 320 due to the RF energy. If the needle 320 is extracted with the skin tissue adhering to the needle 320, the skin may move with the needle 320 when the needle 320 is extracted, thus causing the skin to be torn or causing excessive bleeding.

However, the embodiment of the present disclosure provides positive pressure between the through hole 302 and the skin tissue when or before the needle 320 is removed from the skin tissue, thus preventing the skin from moving with the needle 320 even if the skin tissue adheres to the skin.

It is evident to those skilled in the art that the present disclosure may be materialized in other specific forms without departing from the essential characteristics of the present disclosure. Accordingly, the detailed description should not be construed as being limitative from all aspects, but should be construed as being illustrative. The scope of the present disclosure should be determined by reasonable analysis of the attached claims, and all changes within the equivalent range of the present disclosure are included in the scope of the present disclosure. [Mode for Disclosure]

A handpiece for treatment according to an embodiment of the present disclosure includes a housing having at least one through hole formed in a front end thereof, an insertion portion inserted through a tissue surface of a treatment site into tissue in a state where at least a part of the insertion portion is exposed through the through hole, and a pressure providing channel pulling the treatment site towards the through hole by transmitting negative pressure to a front surface of the through hole, and pushing the treatment site, pulled towards the through hole, away from the through hole by transmitting positive pressure to the front surface of the through hole.

The negative pressure may be formed on the front surface of the through hole through the pressure providing channel so that the insertion portion may be inserted into the tissue simultaneously while the treatment site is pulled towards the through hole or after the treatment site is pulled towards the through hole.

The handpiece may further include a driving portion moving the insertion portion such that a front end of the insertion portion is ejected and retracted through the through hole, and the negative pressure may be formed on the front surface of the through hole through the pressure providing channel, so that the driving portion may move the insertion portion to allow the front end of the insertion portion to be inserted into the tissue simultaneously while the treatment site is pulled towards the through hole or after the treatment site is pulled towards the through hole.

The positive pressure may be formed on the front surface of the through hole through the pressure providing channel so that the insertion portion may be extracted from the treatment site simultaneously while the treatment site is pushed away from the through hole or after the treatment site is pushed away from the through hole.

The handpiece may further include a driving portion moving the insertion portion such that a front end of the insertion portion is ejected and retracted through the through hole, and the positive pressure may be formed on the front surface of the through hole through the pressure providing channel, so that the driving portion may move the insertion portion to allow the front end of the insertion portion to be extracted from the treatment site simultaneously while the treatment site is pushed away from the through hole or after the treatment site is pushed away from the through hole.

The pressure providing channel may include a negative-pressure providing channel providing the negative pressure, and a positive-pressure providing channel providing the positive pressure.

The handpiece may further include a protruding rim formed on the front end of the housing and protruding to surround the through hole, thus defining a treatment-site receiving space, and the pressure providing channel may transmit the negative pressure and the positive pressure to the treatment-site receiving space.

An RF treatment device according to an embodiment of the present disclosure includes a body having an RF generator and a pressure generator, and a handpiece connected to the body. The handpiece includes a housing having at least one through hole formed in a front end thereof, an insertion portion inserted through a tissue surface of a treatment site into tissue and applying RF energy transferred from the RF generator into the tissue in a state where at least a part of the insertion portion is exposed through the through hole, and a pressure providing channel pulling the treatment site towards the through hole by transmitting negative pressure provided by the pressure generator to a front surface of the through hole, and pushing the treatment site, pulled towards the through hole, away from the through hole by transmitting positive pressure provided by the pressure generator to the front surface of the through hole.

The pressure generator may include a negative-pressure generator providing the negative pressure, and a positive-pressure generator providing the positive pressure, and the RF treatment device may further include a first connector transferring the RF energy from the RF generator to the handpiece, a second connector transmitting the negative pressure from the negative-pressure generator to the pressure providing channel, and a third connector transmitting the positive pressure from the positive-pressure generator to the pressure providing channel.

The pressure providing channel may include a negative-pressure providing channel connected to the second connector to transmit the negative pressure provided from the negative-pressure generator to the front surface of the through hole, and a positive-pressure providing channel connected to the third connector to transmit the positive pressure provided from the positive-pressure generator to the front surface of the through hole.

The RF treatment device may further include a protruding rim formed on the front end of the housing and protruding to surround the through hole, thus defining a treatment-site receiving space, and the pressure providing channel may transmit the negative pressure and the positive pressure to the treatment-site receiving space.

The insertion portion may be inserted into the tissue simultaneously while or after the negative pressure provided by the pressure generator is transmitted through the pressure providing channel to the front surface of the through hole.

The handpiece may further include a driving portion moving the insertion portion such that a front end of the insertion portion is ejected and retracted through the through hole, and the driving portion may move the insertion portion to allow the front end of the insertion portion to be inserted into the tissue simultaneously while or after the negative pressure provided by the pressure generator is transmitted through the pressure providing channel to the front surface of the through hole.

The insertion portion may be extracted from the treatment site simultaneously while or after the positive pressure provided by the pressure generator is transmitted through the pressure providing channel to the front surface of the through hole.

The handpiece may further include a driving portion moving the insertion portion such that a front end of the insertion portion is ejected and retracted through the through hole, and the driving portion may move the insertion portion to allow the front end of the insertion portion to be extracted from the treatment site simultaneously while or after the positive pressure provided by the pressure generator is transmitted through the pressure providing channel to the front surface of the through hole.

The handpiece may further include a protruding rim formed on the front end of the housing and protruding to surround the through hole, thus defining a treatment-site receiving space, and the pressure providing channel may transmit the negative pressure and the positive pressure to the treatment-site receiving space.

A method for controlling a treatment device according to an embodiment of the present disclosure includes providing negative pressure between an insertion portion and a tissue surface such that the tissue surface positioned in front of the insertion portion is pulled toward the insertion portion, allowing at least a part of the insertion portion to be inserted into a tissue through the tissue surface, providing positive pressure to the tissue surface such that the tissue surface is pushed away from the insertion portion, and allowing a front end of the insertion portion to be extracted from the tissue surface.

The method may further include transferring RF energy through the insertion portion into the tissue, and the transferring the RF energy may be performed between the providing the negative pressure and the providing the positive pressure.

The allowing the insertion portion to be inserted into the tissue may be performed simultaneously with the providing the negative pressure or after the providing the negative pressure.

The allowing the front end of the insertion portion to be extracted from the tissue surface may be performed simultaneously with the providing the positive pressure or after the providing the positive pressure.

The invention claimed is:

1. An RF treatment device comprising a body including an RF generator, a control unit, a pressure generator, and a handpiece connected to the body, wherein the handpiece comprises:

a housing having at least one through hole formed in a front end thereof, an insertion portion configured to be inserted through a tissue surface of a treatment site into tissue and applying RF energy transferred from the RF generator into the tissue in a state where at least a part of the insertion portion is exposed through the through hole; and a pressure providing channel configured to pull the treatment site towards the through hole by transmitting negative pressure provided by the pressure generator to a front surface of the through hole before applying the RF energy, and configured to push the treatment site, pulled towards the through hole, away from the through hole by transmitting positive pressure provided by the pressure generator to the front surface of the through hole after applying the RF energy, wherein the control unit is configured to control the insertion portion and the pressure generator to move the insertion portion to be extracted from the treatment site, by moving the insertion portion relative to the through hole simultaneously with transmission of the positive pressure provided by the pressure generator through the pressure providing channel to the treatment site, wherein the housing comprises a handpiece body and a tip detachably coupled to the handpiece body, the tip having a base defining a surface to be coupled to the handpiece body, wherein the pressure providing channel includes a negative-pressure providing channel transmitting the negative pressure and a positive-pressure providing channel transmitting the positive pressure, the negative-pressure providing channel and the positive-pressure providing channel being provided in the handpiece body, and wherein end portions of the negative-pressure providing channel and the positive-pressure providing channel each protrude from a recessed surface of the handpiece body.

2. The RF treatment device of claim 1, wherein the pressure generator comprises a negative-pressure generator providing the negative pressure, and a positive-pressure generator providing the positive pressure, and wherein the RF treatment device further comprises:

a first connector transferring the RF energy from the RF generator to the handpiece;

a second connector transmitting the negative pressure from the negative-pressure generator to the pressure providing channel; and a third connector transmitting the positive pressure from the positive-pressure generator to the pressure providing channel.

3. The RF treatment device of claim 2, wherein:

the negative-pressure providing channel is connected to the second connector to transmit the negative pressure provided from the negative-pressure generator to the front surface of the through hole; and the positive-pressure providing channel is connected to the third connector to transmit the positive pressure provided from the positive-pressure generator to the front surface of the through hole.

4. The RF treatment device of claim 3, wherein the control unit is further configured to operate the negative-pressure generator in response to a signal detecting that the tip comes into contact with the treatment site.

5. The RF treatment device of claim 1, further comprising:

a protruding rim formed on the front end of the housing and protruding to surround the through hole, thus defining a treatment-site receiving space,

wherein the pressure providing channel transmits the negative pressure and the positive pressure to the treatment-site receiving space.

6. The RF treatment device of claim 1, wherein the insertion portion is configured to be inserted into the tissue while or after the negative pressure provided by the pressure generator is transmitted through the pressure providing channel to the front surface of the through hole.

7. The RF treatment device of claim 1, wherein the handpiece further comprises a driving portion, and the control unit is configured to control an operation of the driving portion to move the insertion portion such that a front end of the insertion portion is ejected and retracted through the through hole, wherein the driving portion moves the insertion portion to allow the front end of the insertion portion to be inserted into the tissue while or after the negative pressure provided by the pressure generator is transmitted through the pressure providing channel to the front surface of the through hole.

8. The RF treatment device of claim 1, wherein the handpiece further comprises a driving portion, and the control unit is configured to control an operation of the driving portion to move the insertion portion such that a front end of the insertion portion is ejected and retracted through the through hole, wherein the driving portion moves the insertion portion to allow the front end of the insertion portion to be extracted from the treatment site while the positive pressure provided by the pressure generator is transmitted through the pressure providing channel to the front surface of the through hole, wherein the driving portion is configured to move an output terminal in a first direction to eject the front end of the insertion portion through the through hole and configured to move the output terminal in a second direction to retract the front end of the insertion portion through the through hole, and wherein the handpiece further comprises an RF transfer portion in which the insertion portion is installed, the RF transfer portion having a first surface coupled to the output terminal and a second surface coupled to an elastic member, the second surface being opposite to the first surface.

9. The RF treatment device of claim 8, further comprising a support on which a rear surface of the RF transfer portion is configured to be seated, the support being coupled to the base.

* * * * *